(12) United States Patent
Kanowitz

(10) Patent No.: US 9,814,853 B2
(45) Date of Patent: *Nov. 14, 2017

(54) AIRWAY STABILIZATION SYSTEM

(71) Applicant: Securisyn Medical, LLC, Highlands Ranch, CO (US)

(72) Inventor: Arthur Kanowitz, Littleton, CO (US)

(73) Assignee: Securisyn Medical, LLC, Highlands Ranch, CO (US)

( * ) Notice: Subject to any disclaimer, the term of this patent is extended or adjusted under 35 U.S.C. 154(b) by 1052 days.

This patent is subject to a terminal disclaimer.

(21) Appl. No.: 13/924,568

(22) Filed: Jun. 22, 2013

(65) Prior Publication Data

US 2013/0276791 A1 Oct. 24, 2013

Related U.S. Application Data

(63) Continuation-in-part of application No. 13/080,933, filed on Apr. 6, 2011, now Pat. No. 8,739,795, which
(Continued)

(51) Int. Cl.
*A61M 16/04* (2006.01)
*A61M 25/10* (2013.01)
(Continued)

(52) U.S. Cl.
CPC ........ *A61M 16/0497* (2013.01); *A61M 16/04* (2013.01); *A61M 16/0402* (2014.02);
(Continued)

(58) Field of Classification Search
CPC .. A61M 16/00; A61M 16/0003; A61M 16/04; A61M 16/0402; A61M 16/0434;
(Continued)

(56) References Cited

U.S. PATENT DOCUMENTS 3,137,299 A 6/1964 Tabor
3,288,136 A 11/1966 Lund
(Continued)

FOREIGN PATENT DOCUMENTS

DE 19533615 4/1997
DE 19636050 3/1998
(Continued)

OTHER PUBLICATIONS

International Preliminary Report on Patentability Chapter I, dated Aug. 7, 2007.
(Continued)

*Primary Examiner* — Colin W Stuart
(74) *Attorney, Agent, or Firm* — Glenn H. Lenzen; Dietze and Davis, P.C.

(57) ABSTRACT

An airway stabilization system attachable to any airway device to maintain an airway in a patient and which prevents clinically significant movement of the airway device with respect to the patient's vocal cords in response to the application of significant forces in any direction to the device, be they longitudinal, torsional/rotational or bending. The system includes an improved airway device and an improved securing device having interactive components that cooperate integrally with and engage one another to provide unparalleled strength and stability against movement. The securing device includes a unique stabilizer configured to releaseably engage a retention structure on the airway device with a simple twist. A connector device connects the system to a source of ventilatory air without constricting the airway device.

20 Claims, 8 Drawing Sheets

Related U.S. Application Data is a continuation-in-part of application No. 11/346,686, filed on Feb. 3, 2006, now Pat. No. 8,001,969.

(60) Provisional application No. 61/593,702, filed on Feb. 7, 2005, provisional application No. 61/663,366, filed on Jun. 22, 2012.

(51) Int. Cl.
    *A61M 39/10* (2006.01)
    *A61M 16/00* (2006.01)

(52) U.S. Cl.
    CPC ...... *A61M 16/044* (2013.01); *A61M 16/0488* (2013.01); *A61M 16/0493* (2014.02); *A61M 25/1018* (2013.01); *A61M 25/10182* (2013.11); *A61M 25/10184* (2013.11); *A61M 25/10187* (2013.11); *A61M 39/10* (2013.01); *A61M 2016/0027* (2013.01); *A61M 2205/073* (2013.01)

(58) Field of Classification Search
    CPC .......... A61M 16/0463; A61M 16/0475; A61M 16/0488; A61M 16/0493; A61M 16/049; A61M 16/0497; A61M 16/08; A61M 16/0816; A61M 16/0875; A61M 2016/0027; A61M 25/1018; A61M 25/10182; A61M 25/10184; A61M 25/10187; A61M 25/10188; A61M 39/00; A61M 39/10; A61M 2039/1027; A61M 2039/1033
    See application file for complete search history.

(56) References Cited

U.S. PATENT DOCUMENTS

| | | |
|---|---|---|
| 3,602,227 A | 8/1971 | Andrew |
| 3,731,691 A * | 5/1973 | Chen .................. A61M 16/044 128/207.15 |
| 3,760,811 A | 9/1973 | Andrew |
| 3,946,742 A | 3/1976 | Eross |
| 3,987,798 A | 10/1976 | McGinnis |
| 4,056,104 A | 11/1977 | Jaffe |
| 4,235,229 A | 11/1980 | Ranford et al. |
| 4,269,184 A | 5/1981 | Montgomery |
| 4,324,235 A | 4/1982 | Beran |
| 4,341,210 A | 7/1982 | Elam |
| 4,501,273 A | 2/1985 | McGinnis |
| 4,520,813 A | 6/1985 | Young |
| 4,527,559 A | 7/1985 | Roxburg et al. |
| 4,530,354 A | 7/1985 | Froilan |
| 4,548,200 A | 10/1985 | Wapner |
| 4,589,410 A | 5/1986 | Miller |
| 4,622,034 A | 11/1986 | Shattuck |
| 4,658,814 A | 4/1987 | Anderson |
| 4,683,882 A | 8/1987 | Laird |
| 4,744,358 A | 5/1988 | McGinnis |
| 4,774,943 A | 10/1988 | Yu |
| 4,774,944 A | 10/1988 | Mischinski |
| 4,832,019 A | 5/1989 | Weinstein et al. |
| 4,869,718 A | 9/1989 | Brader |
| 4,886,059 A | 12/1989 | Weber |
| 4,953,548 A | 9/1990 | Stoddard et al. |
| 5,009,227 A | 4/1991 | Nieuwstad |
| 5,069,206 A | 12/1991 | Crosbie |
| 5,076,269 A | 12/1991 | Austin |
| 5,251,616 A | 10/1993 | Desch |
| 5,305,742 A | 4/1994 | Styers et al. |
| 5,311,864 A | 5/1994 | Huerta |
| 5,320,097 A | 6/1994 | Clemens et al. |
| 5,341,802 A | 8/1994 | Calebaugh |
| 5,345,931 A | 9/1994 | Battaglia, Jr. |
| 5,353,787 A | 10/1994 | Price |
| 5,368,024 A | 11/1994 | Jones |
| 5,382,239 A | 1/1995 | Orr et al. |
| 5,398,679 A | 3/1995 | Freed |
| 5,402,776 A | 4/1995 | Islava |
| 5,419,319 A | 5/1995 | Werner |
| 5,429,127 A | 7/1995 | Kolobow |
| 5,437,273 A | 8/1995 | Bates et al. |
| 5,443,064 A | 8/1995 | Theis et al. |
| 5,447,152 A | 9/1995 | Kohsai et al. |
| 5,448,985 A | 9/1995 | Byrd |
| 5,490,504 A | 2/1996 | Vrona et al. |
| 5,513,633 A | 5/1996 | Islava |
| 5,551,421 A | 9/1996 | Noureldin et al. |
| 5,555,881 A | 9/1996 | Rogers et al. |
| 5,558,090 A | 9/1996 | James |
| 5,623,924 A | 4/1997 | Lindenman et al. |
| 5,638,814 A | 6/1997 | Byrd |
| 5,653,232 A | 8/1997 | Rogers et al. |
| 5,683,458 A | 11/1997 | Urken |
| 5,699,787 A | 12/1997 | Thompson |
| 5,795,315 A | 8/1998 | Traut et al. |
| 5,803,079 A | 9/1998 | Rogers et al. |
| 5,806,516 A | 9/1998 | Beattie |
| 5,829,430 A | 11/1998 | Islava |
| 5,862,801 A | 1/1999 | Wells |
| 5,868,132 A | 2/1999 | Winthrop et al. |
| 5,894,840 A | 4/1999 | King |
| 5,928,198 A | 7/1999 | Lester |
| 5,934,276 A | 8/1999 | Fabro et al. |
| 5,941,246 A | 8/1999 | Roopchand |
| 5,996,581 A | 12/1999 | Duch |
| 6,010,484 A | 1/2000 | McCormick et al. |
| 6,029,668 A | 2/2000 | Freed |
| 6,050,263 A | 4/2000 | Choksi et al. |
| 6,053,166 A | 4/2000 | Gomez |
| 6,067,985 A | 5/2000 | Islava |
| 6,090,058 A | 7/2000 | Traut et al. |
| 6,105,573 A | 8/2000 | Delaplane et al. |
| 6,105,577 A | 8/2000 | Varner |
| 6,432,085 B1 | 8/2002 | Stellon et al. |
| 6,526,978 B2 | 3/2003 | Dominguez |
| 6,568,393 B2 | 5/2003 | Chrisopher |
| 6,606,991 B2 | 8/2003 | Chou |
| 6,634,359 B1 | 10/2003 | Rudy, Jr. et al. |
| 6,651,666 B1 * | 11/2003 | Owens .................. A61M 16/04 128/204.18 |
| 6,663,581 B1 | 12/2003 | Calabrese |
| 6,668,832 B2 | 12/2003 | Hipolito et al. |
| 6,726,643 B1 | 4/2004 | Martin |
| 6,761,171 B2 | 7/2004 | Toti et al. |
| 6,763,831 B2 | 7/2004 | Sniadach |
| 7,568,484 B2 | 8/2009 | Bierman et al. |
| 7,628,154 B2 | 12/2009 | Bierman et al. |
| 8,001,969 B2 | 8/2011 | Kanowitz |
| 8,739,795 B2 * | 6/2014 | Kanowitz ......... A61M 16/0488 128/207.14 |
| 2002/0069880 A1 | 6/2002 | Lin |
| 2002/0092526 A1 | 7/2002 | Bertoch et al. |
| 2006/0082156 A1 | 4/2006 | Runyan |
| 2012/0247477 A1 * | 10/2012 | Stephenson ........... A61M 16/04 128/207.14 |

FOREIGN PATENT DOCUMENTS

| | | |
|---|---|---|
| EP | 0982045 A2 | 3/2000 |
| GB | 2165157 A | 4/1986 |
| GB | 2340757 A | 3/2000 |
| WO | 80/02645 | 12/1980 |
| WO | 99/33507 | 7/1999 |

OTHER PUBLICATIONS

Dow Corning Corporation, SILASTIC® Endotracheal Tube, Oct. 1971, 2 pages.

Carson et al., The Changing Epidemiology of Mechanical Ventilation: A Population-Based Study. Journal of Intensive Care Medicine. Feb. 2006; 21(3): pp. 173-182.

(56) References Cited

OTHER PUBLICATIONS

Lucas de Silva, Unplanned Endotracheal Extubations in the Intensive Care Unit: Systematic Review, Critical Appraisal, and Evidence-Based Recommendations. Anesth Analg 2012; 114:1003-14.
S.K. Epstein, M.L. Nevins & J. Chung, Effect of Unplanned Extubation on Outcome of Mechanical Ventilation, Am. Journal of Respiratory and Critical Care Medicine, 161: 1912-1916 (2000).
Colice G. L., et al. Laryngeal Injury from Prolonged Intubation: A Prospective Analysis of Contributing Factors. Laryngoscope 2011; 121:596-600. Colice GH, Stukel TA, Dain B. Laryngeal Complications of Prolonged Intubation. Chest. 1989;96:877-884.

\* cited by examiner

AIRWAY STABILIZATION SYSTEM

CROSS-REFERENCE TO RELATED APPLICATIONS

This application is a continuation in part of U.S. Continuation-In-Part patent application Ser. No. 13/080,933 filed on Apr. 6, 2011, which is a continuation-in-part of U.S. patent application Ser. No. 11/346,686 filed on Feb. 3, 2006, now U.S. Pat. No. 8,001,969, which claims priority to U.S. Provisional Application No. 61/593,702, filed Feb. 7, 2005. This application also claims priority to U.S. Provisional Application No. 61/663,366 filed Jun. 22, 2012. The entire disclosures of U.S. patent application Ser. Nos. 13/080,933, 11/346,686, 61/593,702, and 61/663,366 are incorporated herein by reference.

FIELD OF THE INVENTION

The present invention relates generally to a new and improved airway stabilization system designed to maintain an airway in the trachea of a patient. Specifically, the present invention relates to a system for maintaining an airway device in a preselected position in a patient's trachea and for preventing clinically significant movement thereof and unintentional extubation of the patient in response to the application of significant multidirectional forces to the airway device. The system of the present invention is comprised of two components: an improved airway device and an improved securing device. More specifically, the present invention relates to an improved airway device which is configured to prevent unintentional extubation, is anatomically shaped (s-shaped), includes a novel inflation manometer for monitoring and maintenance of balloon pressure in the optimal range, a novel respirator connector which allows for quicker and easier intentional connection and disconnection, and a means of protecting the balloon inflation apparatus from becoming pinched or otherwise damaged during insertion, use and/or removal of the system. The present invention also relates to an improved securing device which is made from a single continuous piece of suitable material for increased strength and an improved securing mechanism of cooperative interaction between the improved airway device and the improved securing device for the purpose of quicker and easier application of the system and resistance against multidirectional forces of a significant magnitude that are applied to the airway device.

BACKGROUND OF THE INVENTION

Endotracheal intubation is a medical procedure used to place an airway device (artificial airway) into a patient's trachea or airway. The use of an airway device is mandated in situations where an individual is unable to sustain the natural breathing function or maintain an open airway on his or her own due to unconsciousness, trauma, disease, drugs or anesthesia. Thus, life-saving mechanical ventilation is provided through the airway device which may be in the form of an endotracheal tube (ETT), or a supraglottic airway device such as a laryngeal mask airway (LMA), King Airway, or one of several other commercially available airway devices.

Endotracheal intubation is accomplished by inserting an airway device into the mouth, down through the throat and vocal cords or voice box, and into the trachea. This procedure creates an artificial passageway through which air can freely and continuously flow in and out of lungs and prevents the patient's airway from collapsing or occluding.

It is very important that the airway device be positioned correctly and maintained in the correct position in the trachea. If the device moves out of its proper position in the trachea and into either the right or left main stem bronchial tube, only one lung will be ventilated. Failure to ventilate the other lung can lead to a host of severe pulmonary complications. Moreover, if the airway device moves completely out of the trachea and into the esophagus, the patient will become hypoxic due to the lack of ventilation to the lungs, a condition which typically results in life-threatening brain injury within a matter of only a few minutes.

Even after an airway device has been positioned correctly, subsequent movement of the patient can lead to inadvertent movement of the device, as hereinabove described. An intubated patient may restlessly move about and may also attempt to forcibly remove an airway device, whether conscious or unconscious, particularly if the patient is uncomfortable or having difficulty breathing, which can lead to panic. Because medical emergencies may occur anywhere, emergency medical service personal (i.e., paramedics) may be called upon to insert airway devices in out-of-hospital emergency settings as well as in hospital settings by emergency department, operating room, and critical care personnel. Therefore, such unintentional movement is not uncommon, particularly when the patient is moved from an out-of-hospital setting, such as an accident scene, to an emergency department of a hospital. Further, anytime an intubated patient may be moved, for example, not only from an ambulance to a trauma facility, but also from one hospital to another hospital, from one area of the hospital to another area in the same hospital (imaging, laboratory, operating theater), or from a hospital to an outpatient rehabilitation facility, unintentional movement of an airway device is a risk. Even repositioning an intubated patient in a hospital bed may cause unintentional movement of the endotracheal tube.

Inadvertent movement of an airway device may also occur as a result of moving external ventilation equipment, such as a conventional mechanical ventilator or bag valve mask, connected thereto where the patient can no longer naturally achieve respiration. Typically, the external ventilation equipment is connected to the external end of the device by an air conduit to establish air flow to and from the lungs. Inadvertent pulling on, or other excessive movement of the air conduit, may transfer movement to the airway device, thereby shifting it from its proper position and causing unplanned extubation.

Unplanned extubation is a hazardous and costly problem which studies have demonstrated occurs at an unacceptably high rate. A study completed by Carson et al reports that approximately 950,000 patients are mechanically ventilated in the United States annually. Carson et al., *The Changing Epidemiology of Mechanical Ventilation: A Population-Based Study. Journal of Intensive Care Medicine.* 2006 February; 21(3): pp. 173-182. A review of the world-wide medical literature suggests that the world-wide rate of unplanned extubation averages approximately 7.31%. Lucas de Silva, *Unplanned Endotracheal Extubations in the Intensive Care Unit: Systematic Review, Critical Appraisal, and Evidence-Based Recommendations.* Anesth Analg 2012; 114:1003-14. Applying the world-wide average to the U.S. figure above, an estimated 68,000 patients in the United States alone experience an unplanned extubation each year. Such unplanned extubations are costly, not only for patients who experience increased rates of morbidity and mortality, but also for hospitals, physicians and insurance companies who incur the liability costs associated therewith. The annual intensive care unit (ICU) bed cost associated with unplanned extubations in the United States alone is estimated at $2.6 M, which includes imaging, pharmacy, and laboratory expenses. (Extrapolated using data from the Carson study referenced above and the cost of long-term care according to the U.S. Department of Health and Human Services National Clearinghouse for long-term care information. See also S. K. Epstein, M. L. Nevins & J. Chung, *Effect of Unplanned Extubation on Outcome of Mechanical Ventilation*, Am. Journal of Respiratory and Critical Care Medicine, 161: 1912-1916 (2000) which discusses the increased likelihood of long-term care outcome). Moreover, it is not unknown for jury damage awards in personal injury law suits arising from unplanned extubations to be in excess of $35 M. The high incidence of unplanned extubation and the associated increase in healthcare costs implies that an improved restraining system, which has the capacity to resist the application of greater forces which would otherwise result in movement of the airway device is sorely needed.

Various prior art systems have attempted to address the problem of maintaining an airway device in the correct position and preventing unintentional extubation. The most common approach for securing an airway device (typically, an endotracheal tube) is with adhesive tape. Umbilical tape may be used as an alternative. Both present the same challenges. The tape is tied around the patient's neck and then wrapped and tied around the smooth outside surface of the endotracheal tube itself. Arranged in this fashion, the tape is intended to anchor the endotracheal tube to the corner of the patient's mouth and prevent its unintentional movement. While the use of tape in this manner provides some benefit, the restraint available from the tape usually diminishes because the tape becomes covered and/or saturated with blood, saliva, or other bodily fluids. Consequently, the endotracheal tube may be readily moved from its preferred position in the patient's trachea, and this form of securing an airway device provides inadequate protection against movement resulting from the application of multidirectional forces such as bending, torsional/rotational or substantial lateral forces to the device. Such forces may exceed fifty (50) pounds in magnitude, and, as shown in the results of two studies of the restraint capabilities of current devices and methods set forth in Tables 1 and 2 below, such devices and methods do not provide sufficient resistance to prevent unplanned extubation. Clinically significant movement is defined as longitudinal movement of the airway device in a direction towards or away from the patient's mouth to a point where the tip of the airway device has moved beyond the vocal cords. Typically, such movement is in the range of five (5) to seven (7) centimeters.

Restraint Capabilities of Current Devices and Methods

TABLE 1

|  | Median | Min | Max |
| --- | --- | --- | --- |
| Thomas Tube Holder | 12.98 | 2.64 | 22.44 |
| Adhesive Tape | 19.58 | 3.96 | 39.6 |
| Non Adhesive Tape | 7.48 | 2.42 | 27.72 |

Force to Extubate (7 cm movement) in Lbs
Owens, et al. Resuscitation (2009)

TABLE 2

|  | Median | Min | Max |
| --- | --- | --- | --- |
| Adhesive Tape (Lillehei) | 19.5 | 15 | 25 |
| Tube Tamer | 12.9 | 10 | 15 |
| Precision Medical | 8.6 | 7 | 10 |
| Biomedix Endogrip | 10.7 | 6 | 12 |
| Thomas Tube Holder | 37 | 28 | 43 |

Force to Extubate (2 cm movement) in Lbs
Carlson, et al. Annals of Emergency Medicine 2007

U.S. Pat. No. 5,353,787 issued Oct. 11, 1994, to Price discloses an apparatus having an oral airway for providing fluid communication for the passage of gas from a patient's mouth through his or her throat and into the trachea, the oral airway being releasably attached to an endotracheal tube for use in combination therewith. While Price's apparatus eliminates the smooth surface of the tube and resists longitudinal movement in relation to the oral airway, the system disclosed by Price does not address the above-identified problem of resisting multidirectional forces. Moreover, Price's device cannot prevent clinically significant movement of an airway device in relation to the vocal cords and an unplanned extubation resulting therefrom.

Other attempts to solve the aforementioned problems have employed auxiliary mechanical securing devices to maintain the position of an endotracheal tube in a patient. Many of these auxiliary mechanical devices include some type of faceplate which is attached to the patient's face, usually with one or more straps that extend around the back of the patient's head or neck. The faceplate includes some type of mechanical contact device that grips the smooth surface of the endotracheal tube. Typical mechanical contact devices include thumb screws, clamps, adhesives, locking teeth, and straps. By way of example, U.S. Pat. No. 4,832,019 issued to Weinstein et al. on May 23, 1989, discloses an endotracheal tube holder which includes a hexagonally-shaped gripping jaw that clamps around the tube after it has been inserted into a patient's mouth and a ratchet-type locking arrangement designed to retain the gripping jaw in position around the tube. Weinstein's patent disclosure states specifically that the tube will not be deformed. However, the fundamental mechanics of a hexagonal receptacle applied around a cylindrical tube to stabilize it reveal that the hexagonal structure will not impart force to the tube of sufficient magnitude to prevent longitudinal movement. As shown in FIG. 1, it has been found that if sufficient pressure is applied directly to the tube by the gripping jaw, the tube will deform or even crush, thereby decreasing ventillatory efficiency to the point that airflow to the patient's lungs will be restricted or even cut off, an extremely serious problem. The outer diameter of a standard 7.5 mm I.D. tube having a cross-sectional area of 44 mm$^2$ is shown at 10. The decrease in cross-sectional area due to deformation or crushing is shown at 15 and is approximately 26.2 mm$^2$. This decrease in cross-sectional area of 40% is the equivalent of using a 4.5 mm I.D. tube.

More recently, U.S. Pat. No. 7,568,484 issued on Aug. 4, 2009, and U.S. Pat. No. 7,628,154 issued on Dec. 8, 2009, both to Bierman et al., disclose endotracheal tube securement systems which include straps extending from the corners of a patient's mouth above and below the patient's ears on each side of the patient's head. However, the devices disclosed in the '484 and the '154 patents merely retain the position of the tube in the patient's mouth and cannot prevent movement thereof in various directions, either longitudinally, rotationally or laterally, as hereinabove described. Moreover, these prior art systems provide no protection for the device itself, inasmuch as the tube is inserted directly into the patient's mouth where it may be pinched or, worse yet, crushed and/or punctured by the biting action of the patient.

Specifically, to maintain an effective restraint, attending medical personnel increase the amount of clamping force applied on an airway device. Increasing the amount of clamping force to an effective level may pinch the device to the point where a portion of the inner tube diameter (and hence air passageway) is significantly restricted. Restricting the cross-sectional size of the air passageway decreases the ventilatory efficiency of the tube, thereby decreasing the respiratory airflow. The restriction of the cross-sectional size of the air passageway creates resistance to both inspiratory airflow and expiratory airflow. Insufficient airflow during inspiration can lead to hypoxemia, which is problematic, but can be overcome by increasing the positive pressure of the ventilation source. However, during expiration, any increased pressure due to constriction or decreased tube diameter, increases the amount of work a patient must perform to simply breathe. Increased pressure can also lead to barotrauma in the lungs and resistance to expiratory airflow can lead to multiple other adverse effects within the lungs. Impairing a patient's ventilations may result in serious medical effects, particularly with patients whose functions are already compromised. Therefore, the ability for clinicians to adequately stabilize an airway device for prevention of unplanned extubation without constriction of the air passageway is crucial for patient safety.

Endotracheal tubes have a standard respiratory connector that serves as a conduit between the endotracheal tube and artificial ventilator for the purpose of maintaining a continuous flow of air from the ventilation source to the patient's lungs. Standard connectors must be deeply seated into the endotracheal tube to avoid unintentional disconnection of the ventilation source from the endotracheal tube during mechanical breathing. When deeply seated, the connector is often difficult for the clinician to remove the endotracheal tube. Therefore, an airway device with a connector that prevents unintentional disconnection, yet allows for quick and easy intentional connection and disconnection is needed.

In addition to having a securement system which provides effective restraint of the entire airway stabilization system, the endotracheal tube element of the system may also include an inflatable balloon positioned at the distal end thereof. Inflation of the balloon helps secure the distal end inside the patient at a preselected depth in the airway and prevents the movement of fluids into the lungs. Most endotracheal tubes use an airline having one end directly attached to the balloon and the other end attached to an external inflation device for selectively inflating the balloon and maintaining a desired level of inflation pressure. The inflation tube is typically very small in diameter, perhaps no larger than a millimeter, and runs along the outside circumference of the endotracheal tube from the externally positioned inflation device down into the patient's trachea to the balloon. It is fragile and, in its exposed position, is susceptible to being pinched, broken and/or cut. If the integrity of the inflation tube is compromised by cutting, pinching, breaking or any other destructive mechanism, the balloon is unable to maintain inflation pressure and therefore becomes no longer effective at preventing the aspiration of fluids into the lungs, which may cause pneumonia and/or other serious medical complications. For maximum patient safety, cuff pressures should be maintained between 20 and 30 cm $H_2O$. Balloon pressure below 20 cm $H_2O$ does not adequately protect a patient's airway from fluid aspiration. Pressures above 30 cm $H_2O$ exceed capillary perfusion pressures and thus can lead to tissue injury, or necrosis. Therefore, the market calls for a novel airway device with built-in features for monitoring and maintenance of balloon pressure in the optimal range and for protecting the balloon inflation apparatus from becoming pinched or otherwise damaged during insertion, use and/or removal of the system.

Moreover, endotracheal tubes are historically c-shaped. Due to the elastomeric properties of the material from which an endotracheal tube is formed, the tendency of an endotracheal tube is to return to its original c-shape after it is deformed. The human anatomy from the oral opening to the vocal chords and into the trachea is s-shaped. When a c-shaped endotracheal tube is inserted into an s-shaped airway using a stylet, the tube returns to its original shape once the stylet is removed, and pushes against various portions of the patient's airway (i.e. lips, tracheal wall, vocal cords). Research has shown clearly that the vast majority of intubated patients experience redness and swelling of the vocal cord region and between 36 and 74 percent experience actual ulceration of esophageal tissue. House J C, et al. *Laryngeal Injury from Prolonged Intubation: A Prospective Analysis of Contributing Factors*. Laryngoscope 2011; 121: 596-600. Colice G H, Stukel T A, Dain B. *Laryngeal Complications of Prolonged Intubation*. Chest. 1989; 96:877-884. Accordingly, a need exists for an anatomically shaped endotracheal tube which would apply less pressure to the adjacent tissue and reduce or eliminate the irritation and/or ulceration observed as noted above.

In view of the above, it will be apparent to those skilled in the art from this disclosure that a need exists for an improved airway stabilization system which not only protects an airway device from occlusion and crushing, but also is easier to apply to a patient while at the same time maintains the device in its preferred position in a patient's trachea and prevents clinically significant movement thereof with respect to the vocal cords as a result of the application of multidirectional forces of significant magnitude thereto. Moreover, a need also exists for an airway stabilization system that is structured to protect an inflation system for a balloon positioned at a distal end of an airway device from pinching, breakage and/or cutting and which is anatomically shaped to prevent irritation and/or ulceration of adjacent tissues. The present invention addresses these needs in the art as well as other needs, all of which will become apparent to those skilled in the art from the accompanying disclosure.

SUMMARY OF THE INVENTION

In order to achieve the above-mentioned objectives and other objects of the present invention, a complete airway stabilization system is provided which may be fitted to any airway device to maintain an airway in a patient's trachea and which prevents clinically significant movement of the airway device with respect to a patient's vocal cords in response to the application of forces in any direction to the device, be they longitudinal, torsional/rotational or bending.

Unlike conventional prior art devices which employ a passive airway device, for example, an endotracheal tube and an active stabilizer, the system disclosed herein comprises an improved airway device and improved securing device having at least two interactive components that cooperate integrally with and engage one another to provide unparalleled strength and stability against movement, even when the endotracheal tube becomes slippery from fluids and/or secretions. Moreover, the system of the instant invention provides the above-referenced strength and stability without applying constricting pressure to the airway device itself. The airway device has a continuous sidewall extending between a proximal and a distal end portion thereof which defines a hollow conduit through which the airway is established. A retention collar positioned on to the airway device on the exterior of the sidewall between the end portions thereof. The retention collar may also be formed integrally with the airway device. The retention collar extends along a predetermined length of the sidewall at a predetermined fixed position relative to the distal end to locate the retention collar adjacent to the mouth of the patient within a bite block when the distal end of the airway device is positioned in the trachea to establish the airway. The retention collar includes a plurality of restraints extending circumferentially about the collar. The restraints provide an active surface area forming a tight interlocking fit with cooperating interlocking portions of a securing device secured to a patient, thereby establishing a complete barrier against movement which would otherwise result from forces applied to the device as hereinabove described.

A securing device includes a stabilizing device which is secured to the patient and is configured to releasably engage the retention structure to prevent clinically significant movement of the distal end of the airway device with respect to the vocal cords of the patient in response to various multi-directional loads or forces of a significant magnitude which may be applied to the airway device during movement of the patient or by the patient himself. Unlike prior art devices, the stabilizing device is formed of a single member to allow greater ease of application, includes an annular disc member and bite block having an aperture formed therein of a predetermined configuration structured and arranged to interact with the restraints on the retention collar to maintain the airway device in its preferred position. The bite block extends circumferentially around the retention structure and into the patient's oral cavity to prevent pinching or crushing of the airway device. The stabilizer slides easily onto the airway device; it is simply rotated to lock it into position.

In an embodiment, an endotracheal tube assembly is provided that comprises a respiratory connector, a central connector and a tubular member. The respiratory connector has an annular flange and a connector portion extending from the flange. The central connector has a proximal end portion and a distal end portion. The proximal end portion and the respiratory connector are in a removably attachable configuration. The tubular member is removably attached to the distal end portion of the central connector. The tubular member includes a wall section having a lumen therein, an inflatable balloon at one end thereof, a novel balloon inflation system including a manometer for monitoring and maintaining balloon pressure, and means for preventing damage to the inflation system.

In yet another embodiment, an endotracheal tube is provided which has an anatomically correct shaped configuration to properly align the tube with the normal curvatures of the human airway.

These and other objects, features, aspects and advantages of the present invention will become apparent to those skilled in the art from the following detailed description of preferred embodiments taken in connection with the accompanying drawings, which are briefly summarized below, and by reference to the appended claims.

BRIEF DESCRIPTION OF THE DRAWINGS

Referring now to the attached drawings which form a part of this original disclosure.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
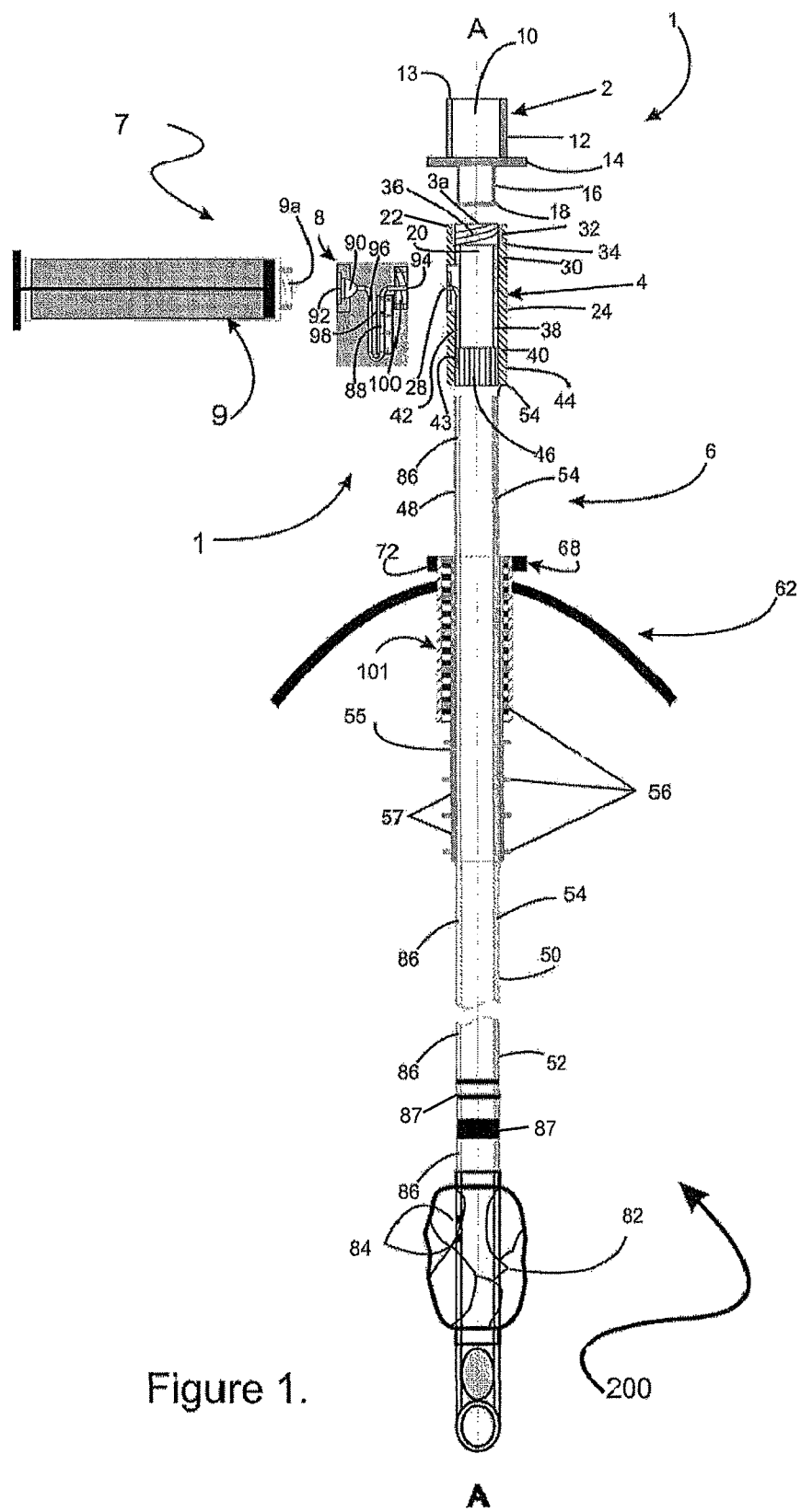
FIG. 1 is a partial cross sectional exploded view of an airway stabilization system according to an embodiment of the present invention.

Referring initially to FIG. 1, an airway stabilization system 200 including an airway device, by way of example, an endotracheal tube assembly 1, is illustrated in accordance with an embodiment of the present invention. The endotracheal tube assembly 1 includes a respiratory connector 2, a central or main connector 4, a tube member 6 having a preselected external and internal diameter, and an inflation system shown generally at 7 including an inflation manometer 8. The respiratory connector is preferably in the form of a standard, 15 mm connector 2, as is well known in the art, is easily attachable and detachable, does not constrict the internal diameter of the tube member, and is required by applicable standards for use in airway applications. However, standard connectors of other sizes may also be employed in various configurations of the system of the present invention without departing from the scope hereof. The respiratory connector 2 is removably attached to the central connector 4, which, as will be discussed in greater detail below, may be press fit into the central connector, may be in the form of a threaded fit, may include a threaded Luer-lock end 18 to facilitate installation and removal thereof from an end 3a of the central connector having a female Luer-lock threaded end adapted to receive end 18, or any other type of fit, as applicable. The central connector 4 is secured to the tube member 6 and directs air or oxygen toward the tube member 6.

The inflation manometer 8 is removably attached to, or integral with the central connector 4 and directs air from an external source into the inflation lumen of the central connector. By way of example and not of limitation, the external air source may be in the form of an inflation syringe 9 which may be easily attached via a threaded connector 9a to either the manometer 8 or directly to the central connector 4 via an inflation system receptacle 28. Alternatively, the inflation manometer may be permanently secured to the system as part of the entire assembly, or integrally formed as part of the system, for use in clinical or hospital environments.

The respiratory connector 2 and the central connector 4 are preferably made of a rigid biocompatible polymer. Rigid biocompatible materials may include blends of polycarbonate, ABS, polyether imide or PVC with a higher durometer or combinations thereof. The tube member 6 is preferably made of a flexible biocompatible polymer. For example, flexible materials including blends of PVC, polyurethane and silicone or combinations thereof may be used.

The respiratory connector 2 is a rigid tubular member with an air passage 10 running therethrough and provides a connection for various medical devices, by way of example, a breathing assist system (bag-valve mask ventilator or mechanical ventilator). The respiratory connector 2 includes an outlet portion 12, a flange portion 14 and a connector portion 16. The outlet portion 12 has a tubular wall 13 with an inner diameter larger than the connector portion 16 and a standard 15 mm outer diameter. The flange portion 14 is an annular portion that extends radially outward from the outlet portion 12 so as to have an outer diameter larger than the outlet portion 12. The connector portion 16 extends distally from the flange portion 14 and includes a threaded section 18. In this embodiment, the threaded section 18 includes male threads for connection with the central connector 4. The connector portion 16 is a rigid tubular member with the air passage 10 running therethrough.

Figure 4:
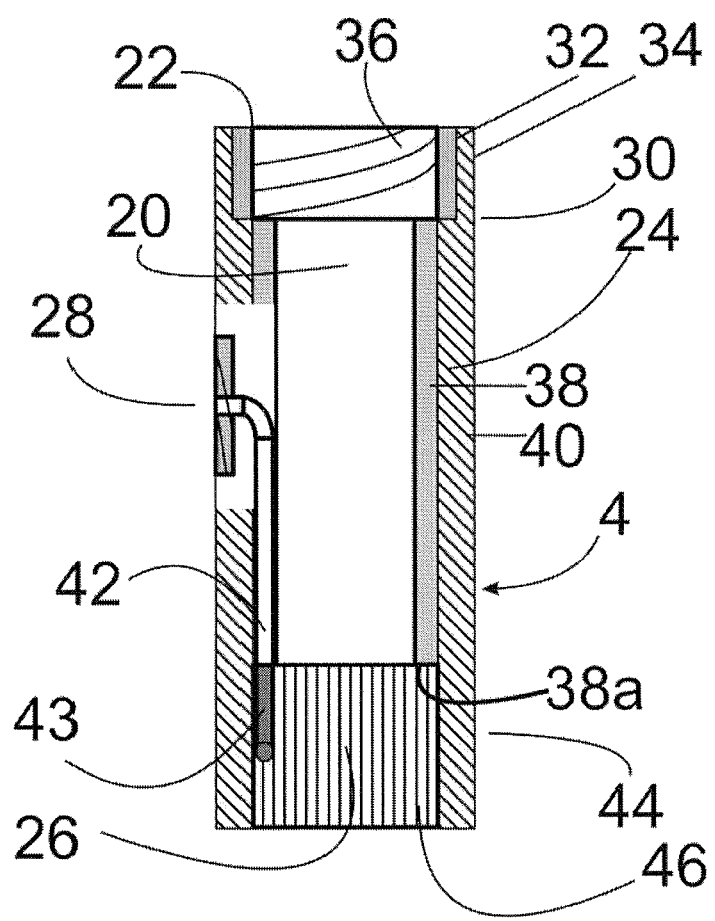
FIG. 4 is a side cross sectional view of a central connector of the airway stabilization system according to an embodiment of the present invention.
Figure 7:
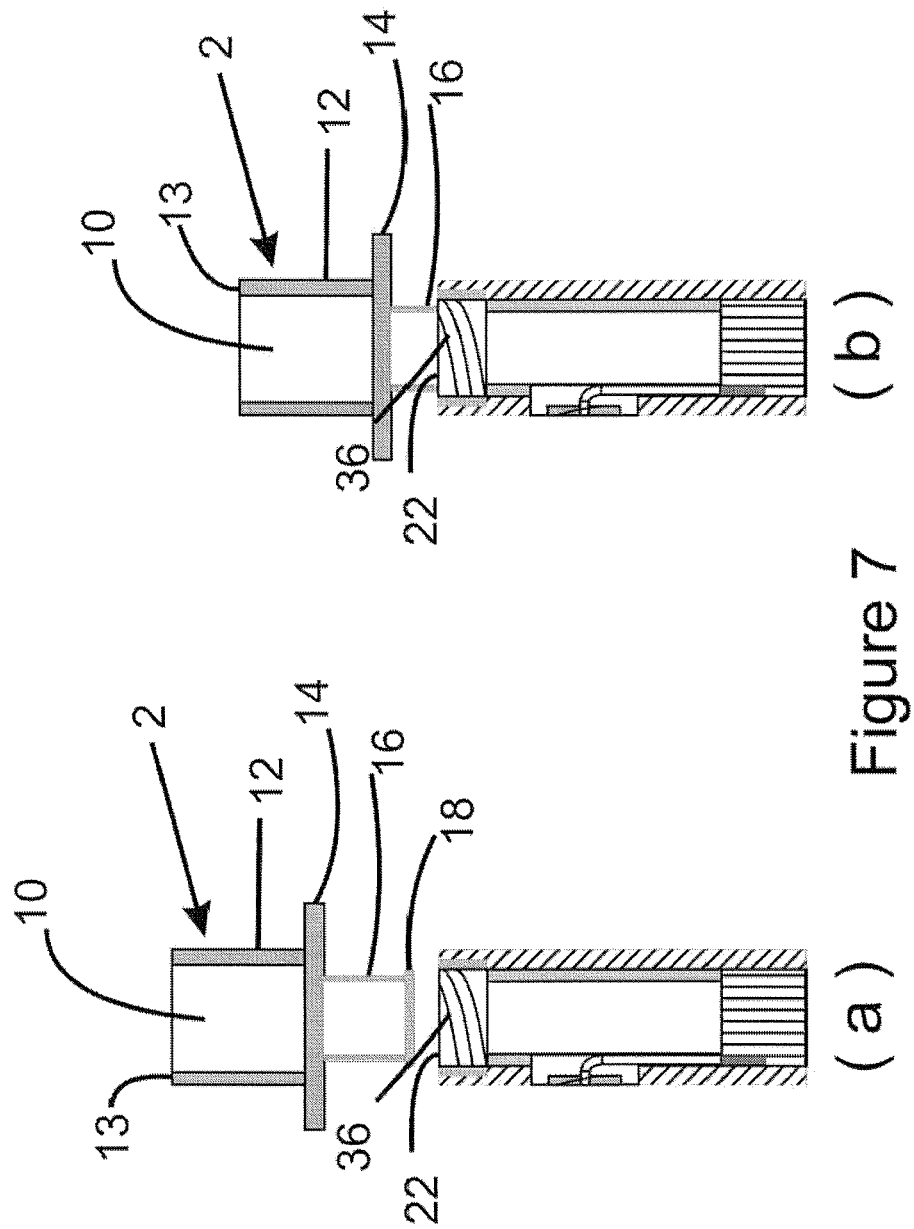
FIGS. 7(a) and 7(b) are side cross sectional views of a removable respiratory connector being positioned over and secured to the central connector in accordance with an embodiment of the resent invention.

Referring now to FIG. 4 and FIG. 7, the central connector 4 is a rigid tubular member that connects the first air passage 10 of the respiratory connector with a second air passage 20 and serves as a conduit for inserting ventilatory air or oxygen into the tube member 6. The central connector 4 includes an attachment portion 22, a body portion 24, and an inflation system receptacle 28. The attachment portion 22 is at a proximal end portion 30 of the central connector 4 and is configured to mate with the connector portion 16 of the respiratory connector 2. The attachment portion 22 includes an inner wall section 32 and an outer wall section 34. The inner wall section 32 is disposed against the inside of the outer wall 34. In some embodiments, the inner wall section 32 and the outer wall section 34 form an integral, unitary, one-piece wall section. The inner wall section 32 has a threaded section 36 with female threads sized to mate with the threaded section 18 of the respiratory connector 2. As discussed above, the connection of the threaded section 18 and the threaded section 36 can be a Luer-lock connection with a Luer taper. That is, the threaded section 18 can be a male taper connection fitting and the threaded section 36 can be a mating female connection of the Luer-lock type.

The body portion 24 is connected to the attachment portion 22 and is disposed distally from the attachment portion 22. The body portion 24 has a tubular shape with an exterior diameter substantially the same as the attachment portion 22. The body portion 24 of the central connector 4 includes an inner wall section 38 and an outer wall section 40. The inner wall section 38 is disposed against an inside of the outer wall section 40. The inner wall section 38 includes an inflation system lumen 42 therein that extends axially within the inner wall section 38 towards the receptacle portion 26 at a distal end portion 44 of the central connector 4.

The outer wall section 40 forms a receptacle aperture 46 at the distal end portion 44. The receptacle aperture 46 is sized and configured to removably receive the tube member 6, and may be configured to be a press fit, a threaded fit, a threaded Luer-lock or any other type of applicable fit. The receptacle aperture 46 is structured and arranged to accommodate the variations in the dimensions of various sizes of endotracheal tubes due to manufacturing tolerances (see Table 3 below) and, thus, allows for installation of the connector without restricting the interior diameter of the tube.

TABLE 3

| ETT ID | Connector ID Inches | mm | −.08 mm | +.08 mm |
|---|---|---|---|---|
| 6 | 0.236 | 5.9944 | 5.9144 | 6.0744 |
| 6.5 | 0.257 | 6.5278 | 6.4478 | 6.6078 |
| 7 | 0.276 | 7.0104 | 6.9304 | 7.0904 |
| 7.5 | 0.297 | 7.5438 | 7.4638 | 7.6238 |
| 8 | 0.315 | 8.001 | 7.921 | 8.081 |
| 8.5 | 0.335 | 8.509 | 8.429 | 8.589 |
| 9 | 0.354 | 8.9916 | 8.9116 | 9.0716 |

The inflation system receptacle 28 is an opening formed in the body portion 24 of the central connector 4 and is connected to the inflation system lumen 42 to allow air passage into the inflation system lumen 42 and then into a central connector inflation system cannulation needle 43. The inflation system receptacle 28 extends through the outer wall section 40 to the inner wall section 38, but does not extend through the inner diameter of the inner wall section 38 and is isolated from the air passage 10. The inflation system receptacle 28 includes threads for mating with either the inflation manometer 8 or with the inflation syringe 9 via threaded connector 9a. In other embodiments, the receptacle 28 is sized and configured to mate with an inflation manometer, syringe or other source of air via a Luer connection as hereinabove described.

Figure 5:
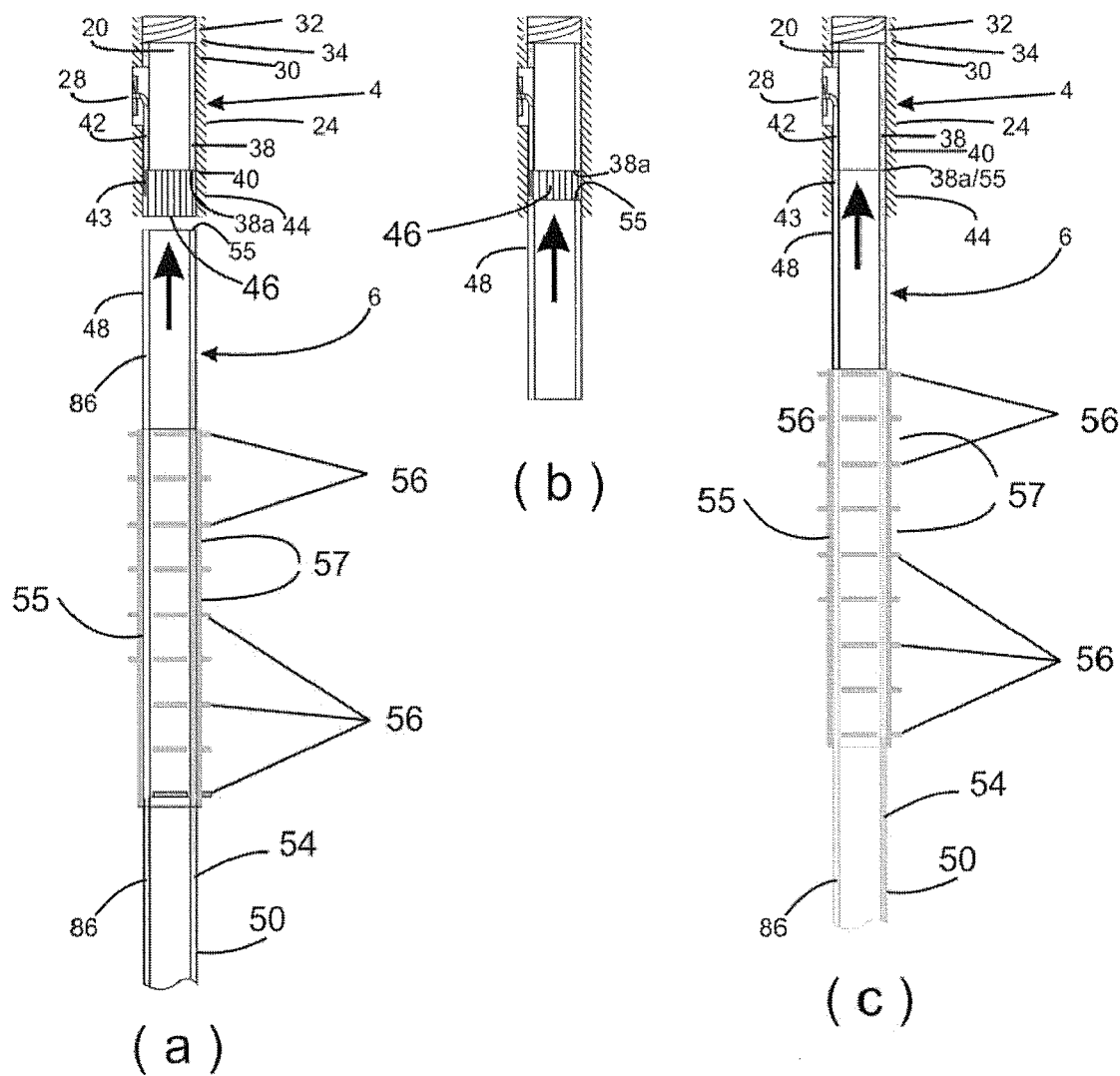
FIGS. 5(a), 5(b) and 5(c) are side cross sectional views of stages of the central connector being positioned over and secured to an end of an endotracheal tube assembly in accordance with an embodiment of the present invention.

Referring now to FIG. 5, the tube member 6 is a flexible member with a tubular shape extending along an axis A. The tube member 6 includes a proximal end portion 48, an elongate body portion 50 having preselected internal and external diameters, a distal end portion 52 and a wall section 54. The proximal end portion 48 is sized and configured to mate with the distal end portion 44 of the central connector 4 by fitting within a tube receptacle aperture 46 formed in the end portion 44. The inner wall section 38 of the central connector 4 is sized and configured to form a face 38a which, in turn, is structured and arranged to abut a proximal face 55 of the wall section 54 of the tube member 6. The outer diameter of the wall section 54 fits against the inner diameter of the outer wall section 40 of the central connector 4, and the tube member and the central connector may be secured together by chemical bonding or other suitable joining techniques.

Figure 2:
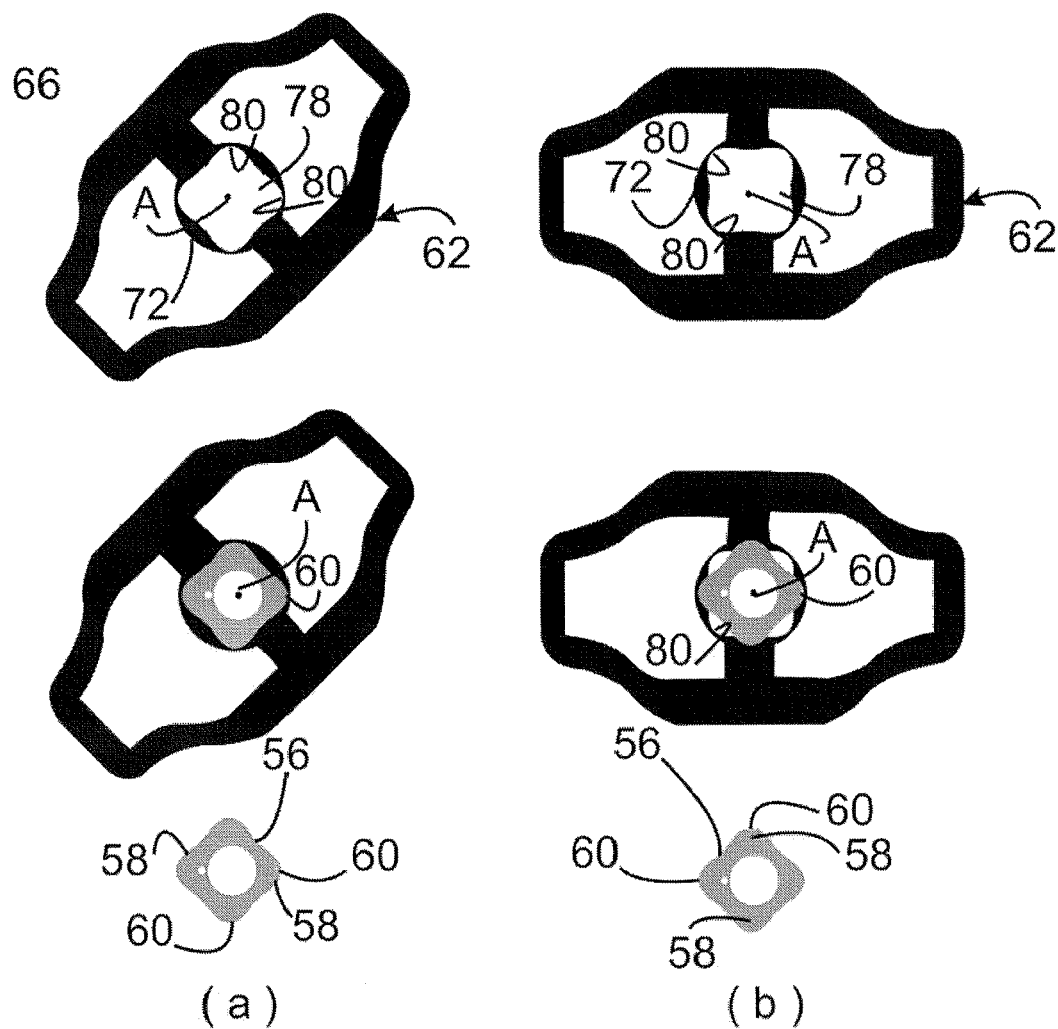
FIGS. 2(a) and 2(b) are top plan views of a stabilizing device of the present invention shown in an aligned, unlocked position and a locked position along an endotracheal tube assembly respectively according to an embodiment of the present invention.

Referring to FIG. 1 and as shown in greater detail in FIG. 2 and FIG. 5, the elongate body portion 50 connects the proximal and distal end portions 48 and 52. The elongate body portion 50 includes a retention member or collar 55 extending circumferentially about the body portion coaxially therewith and disposed at a preselected position thereon and having a plurality of ribs 56 formed therein and extending radially outwardly therefrom in the form of an annular flange. The retention collar may be formed integrally with the tube member 6 or may be secured thereto by chemical bonding or other suitable means. The ribs 56 are positioned axially along the length of the retention collar 55, there being a uniform or substantially uniform distance between each of the ribs forming spaces or structural recesses 57 therebetween. Each rib 56 includes multiple lobes 58 that extend radially from the collar, each lobe 58 forming an arcuate section between an adjacent lobe. Accordingly, each rib comprises multiple lobes 58 with multiple arcuate sections therebetween. At its tip 60, the lobe 58 has a maximum radius from an axis A of the elongate body portion 50. Between peaks 60 of the lobes 58, the radius from the axis A decreases until the radius is substantially the same radius as the exterior of the elongate body portion 50. The lobe 58 has a shape such that the radius from the axis A to an exterior of the lobe 58 gradually increases and then decreases to substantially the same radius as the exterior of the elongate body portion 50.

Figure 3:
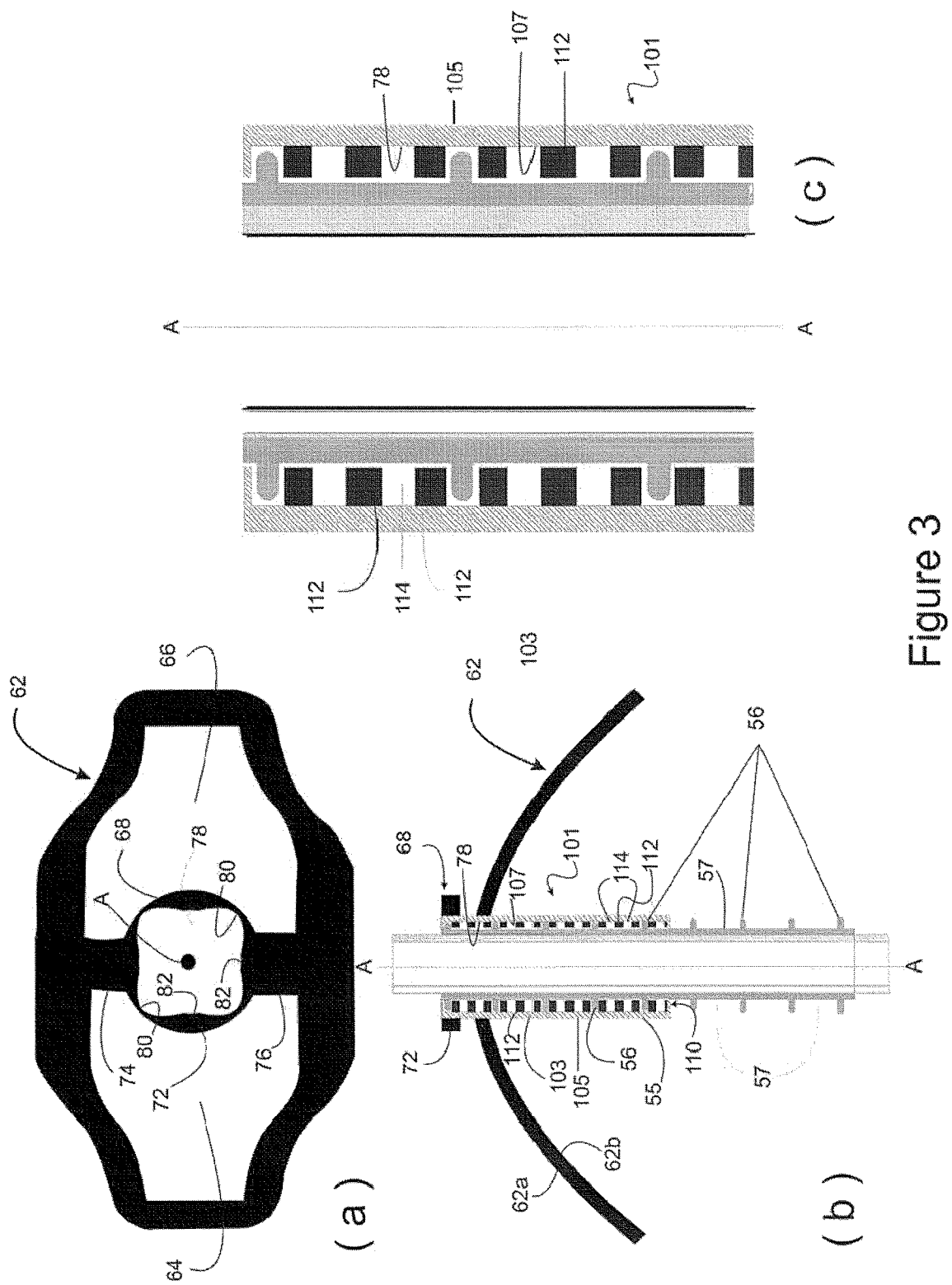
FIGS. 3(a), 3(b), and 3(c) are an enlarged top elevation view and side sectional views of a portion of FIG. 1 respectively showing the engagement of a stabilizing device and bite block according to an embodiment of the present invention.

Referring now to FIGS. 3a, b and c, a securing device or stabilizer 62 adapted to be secured to a patient is illustrated in greater detail. The stabilizer 62 is structured and arranged to actively engage the retention collar 55 and to cooperate therewith to prevent clinically significant movement of the airway device with respect to a patient's vocal cords in response to the application of forces of a significant magnitude thereto. It includes an upper surface 62a and a lower surface 62b and is formed of a single piece of suitable material, for example, a flexible biocompatible polymer. Other flexible materials including blends of PVC, polyurethane and silicone or combinations thereof also may be used. The stabilizer includes first and second apertures 64 and 66 separated by a support member 68 disposed therebetween. The apertures permit access to the patient's face, mouth and oral cavity for administering medications and hygiene. The support member 68 includes a generally circular disc member 72 and first and second coupling members 74 and 76, all integrally formed in the stabilizer. As shown more clearly in FIG. 3b, the disc 72 is supported by coupling members 74 and 76 at a level slightly above the upper surface 62a of the stabilizer to provide clearance for a patient's lips, resulting in enhanced comfort. The stabilizer 62 is configured to receive the tubular member 6 and retain the tubular member 6 at a desired position in a patient's mouth and may be bent so as to curve around and conform to a patient's face. It may be held in place by an elastomeric strap or other suitable retention means adapted to be releasably secured about a patient's head.

The stabilizer 62 includes an aperture 78 formed substantially symmetrically about axis A therein and extending therethrough having substantially the same multiple lobe configuration including a plurality of arcuate spaced-apart sections forming radially outwardly extending peaks 80 separated by arcuate lobe hollows or recesses 82, the peaks and recesses being structured and arranged to form a mirror image shape of the shape of each of the ribs 56 or the retention collar 55. The peaks 80 are sized, configured and arranged to allow the lobes 58 to slide therethrough when the stabilizer is rotated approximately 45 degrees in either direction with respect to the retention collar. The peaks 80 are spaced to accommodate the spacing of the lobe tips 60 disposed about the retention collar 55. When either the stabilizer or the tube assembly 6 having the retention collar secured thereto is rotated so as to align the tips 60 with the peaks 80, the tube member 6 can slide through the disc member 72. When they are rotated relative one to another into a position in which the tips 60 are between the peaks 80, the tips operatively engage the lobe recesses 82 and the disc member 72 is secured between the ribs 56. Thus, because one or more of the tips 60 abut and engage the disc member 72 between the peaks 80, the tube member 6 is prevented from sliding through the disc member 72 and is locked in a preselected position with respect to a patient's vocal cords, depending upon the size of a patient's airway. Other stabilizers, such as those disclosed in U.S. Pat. No. 8,001,969 and U.S. patent application Ser. No. 13/080,933, can be used with the lobe hollow 78 extending therethrough.

Referring to FIGS. 3b and 3c, the stabilizer 62 further includes a hollow generally cylindrically shaped member or bite block 101 extending in a substantially perpendicular direction from the bottom surface 62b along and parallel to axis A. The bite block includes a body portion 103 having an outer surface 105 and inner surface 107, the body portion and inner surface defining a cylindrically shaped cavity 110 about axis A. The body portion includes a plurality of spaced apart annular flanges or ribs 112 extending substantially radially inwardly from the inner surface 107 thereof, each annular flange cooperating with an adjacent annular flange to define a structural recess 114 disposed therebetween. Each rib 112 has an aperture 78 formed therein of substantially the same configuration, alignment and orientation about axis A as the aperture 78 formed in disc member 72. Each aperture 78 is adapted to receive the tube assembly 6 in the same manner as described above with respect to aperture 78 in disc 72. The inwardly-extending ribs and structural recesses of the bite block are structured and arranged to releasably engage corresponding mating spaces 57 and outwardly-extending ribs 56 of the retention collar to interlock with one another when the tube number is rotated into a position as described above in which the tips 60 are between the peaks 80. In the locked position, multiple points of contact and interaction between the stabilizer and the retention collar 55 are created which prevent clinically significant movement of the airway device in response to substantial forces which may be applied thereto in any direction.

The bite block is adapted to be removably inserted into the patient's mouth. Unlike prior art systems which clasp the tube of the airway device directly and focus on preventing movement resulting from single direction longitudinal forces, the restraining apparatus of the instant invention completely encapsulates the airway device, not only isolating it totally from any pinching or crushing forces, but also securing it against movement resulting from the application of torsional/rotational, bending and longitudinal forces which may be applied, as well.

Referring back to FIG. 1, a novel inflation system is depicted generally at 7. It includes a balloon 82 and at least one inflation system balloon aperture 84 at the distal end portion 52 of the tube assembly 6. The balloon 82 has a flexible outer layer and is inflatable and deflatable as desired. The balloon aperture extends through the wall section 54. The wall section 54 includes an inflation lumen 86, more clearly shown in FIG. 5. The central connector inflation lumen 42 connects with the tube inflation lumen 86 via cannulation needle 43 of the central connector 4 to provide a conduit for air used to inflate the balloon. The inflation lumen 86 extends along a length of the elongate body portion 50 and the distal end portion 52 in the wall section 54 and is formed integrally with the body portion, which protects the inflation system, and, specifically, the lumen portion thereof, from damage during insertion, use and removal of the airway system in a patient. At least one ingress aperture 84 extends through the wall section 54 to the inflation lumen 86 and provides a passage for inflation air into the interior of the balloon 82.

Figure 6:
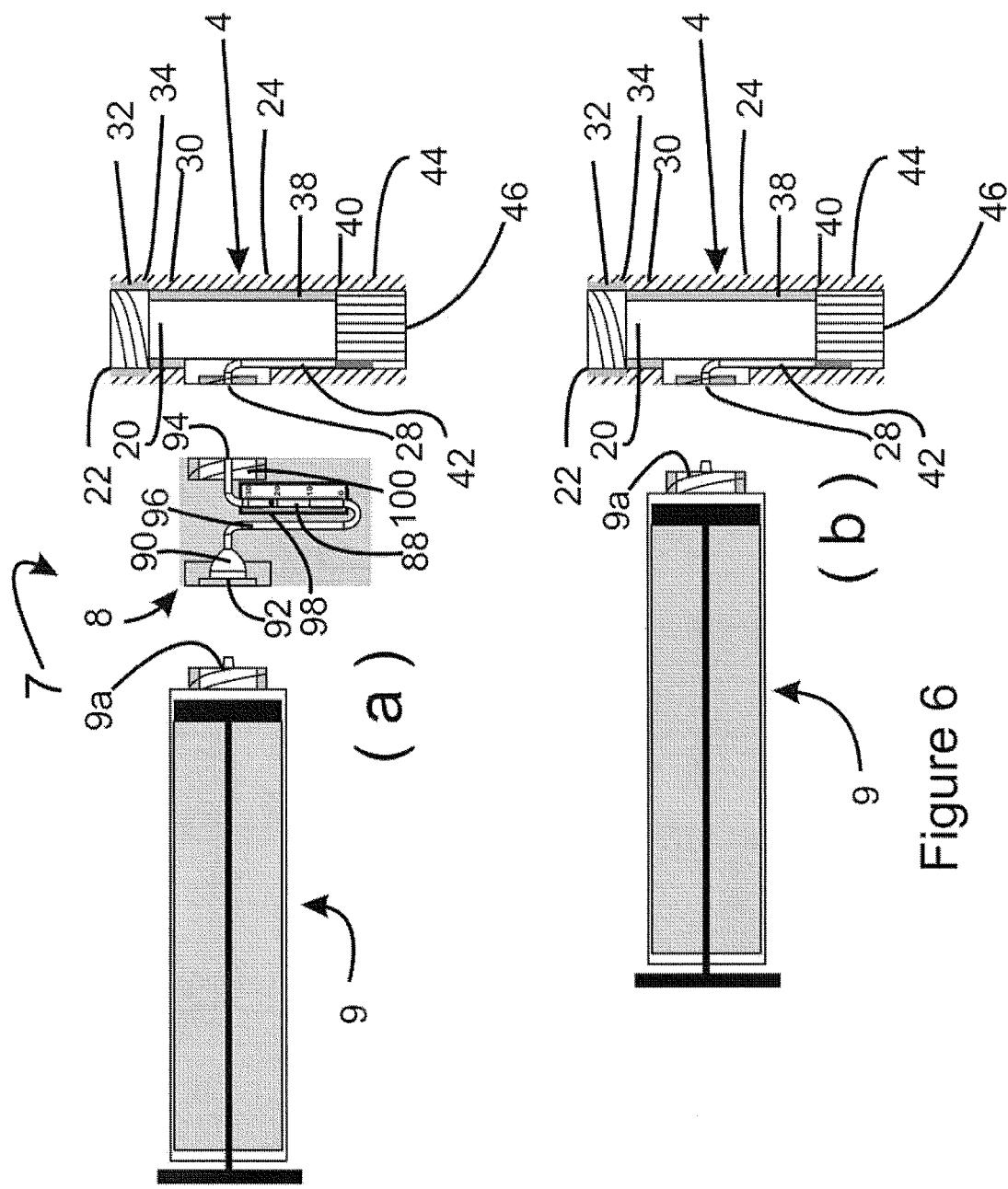
FIGS. 6(a) and 6(b) are side cross sectional views of inflation systems in accordance with embodiments of the present invention.

Referring back to FIG. 6, the inflation system further includes an inflation manometer 8 having a pressure sensor 88, a one-way valve 90, an inlet portion 92, an outlet portion 94 and a conduit portion 96. The pressure sensor 88 is connected to the one-way valve 90 and the conduit portion 96. The inlet portion 92 is sized and configured to receive a nozzle from a pump or a syringe and preferably provides an air tight connection with the nozzle. The pressure sensor 88 senses the pressure in the conduit portion 96. In this embodiment, the pressure sensor 88 includes a display 98 to monitor the pressure in the conduit portion 96. The display 98 can be analog or digital.

The conduit portion 96 runs between the inlet portion 92 and the outlet portion 94. The outlet portion 94 includes a fastening section 100 that is removably attachable to the inflation system receptacle 28 forming an air-tight connection. The fastening section 100 may include a male taper connection fitting such as that in a Luer-lock. The conduit portion 96 is fluidly connected with the central connector lumen 42, the inflation lumen 86 and the interior of the balloon 82 via the inflation system balloon aperture 84. Therefore, the pressure within the balloon 82 can be monitored with the pressure sensor 88.

In structure and operation, the novel inflation system 7 of the present invention provides an inflation line via inflation lumen 86 that is directly accessible by either the syringe 9 or the inflation manometer 8. The lumen is totally enclosed, thereby preventing potential damage thereto such as the pinching, cutting or tearing experienced in the use of prior art inflation devices—all of which may render the tube assembly unusable.

The inflation manometer 8 facilitates the ability of a clinician to maintain the pressure in the balloon 82 at the optimal pressure range of 20-30 cm of water to prevent the undesirable results of obstructed blood flow caused by too high a pressure (ischemia, infarction cascade, neurotic tissue leading to ulceration, fissures, and the like). In contrast, too low a pressure can lead to fluid aspiration into the lungs and an increased likelihood of extubation.

Figure 8:
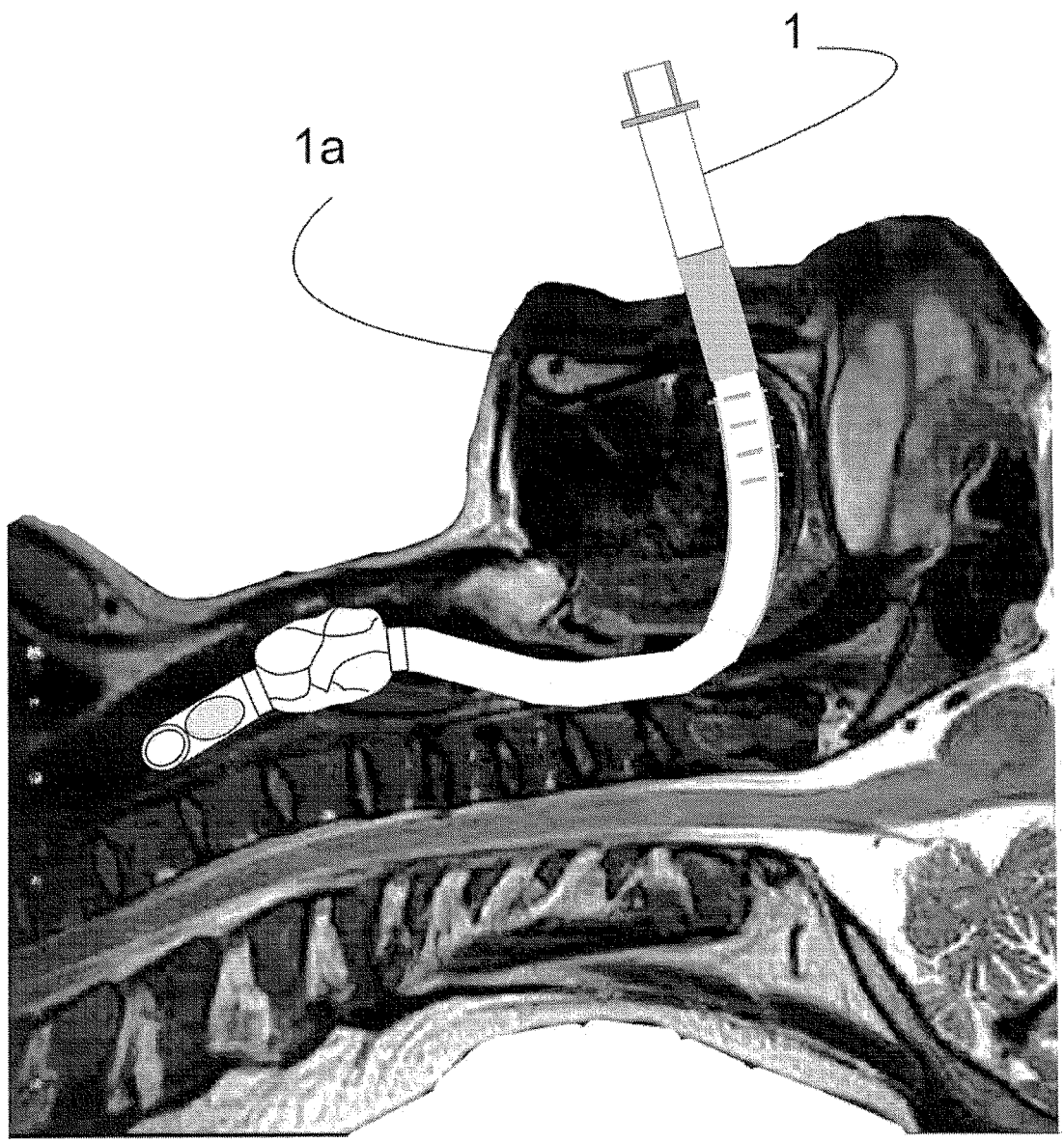
FIG. 8 is a partial cross sectional view of an MRI image of a patient showing the installation of an airway stabilization system in the patient's airway in accordance with an embodiment of the present invention.

Referring now to FIG. 8, a MRI cross sectional image of a patient 1a is shown having the airway device 1 of the present invention inserted in the patient's airway. Endotracheal tubes are historically c-shaped. Due to the elastomeric properties of the material from which they are formed, the tendency of conventional endotracheal tubes is to return to their original shape after they are deformed. The human anatomy from the oral opening to the vocal chords and into the trachea is s-shaped. When a c-shaped endotracheal tube is inserted into an s-shaped airway using a stylet, once the stylet is removed, the tube returns to its original shape and pushes against various portions of the esophagus, primarily in the region of the vocal cords. Research has shown clearly that the vast majority of intubated patients experience redness and swelling of the vocal cord region and between 36 and 74 percent experience actual ulceration of esophageal tissue. Accordingly, the airway stabilization system 200 of the present invention includes an anatomically shaped (s-shaped) endotracheal tube 1 which would apply less pressure to the adjacent tissue following installation and reduce or eliminate the irritation and/or ulceration observed from the use of prior art devices.

GENERAL INTERPRETATION OF TERMS

In understanding the scope of the present invention, the term "configured" as used herein to describe a component, section or part of a device that is constructed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An airway stabilization system for maintaining an airway device in a patient's trachea, the patient having a head, a face, a mouth, lips, an oral cavity, vocal cords, a neck, a chest and a chin, the system comprising:

an s-shaped tubular airway device adapted to conform anatomically to the patient's trachea, the airway device including an elongate body portion having internal and external diameters extending along a central axis, a proximal end, a distal end and a continuous sidewall extending between the proximal and distal ends;

a respiratory connector adapted to connect the s-shaped tubular airway device to an external source of ventilatory air;

a central connector adapted to connect the respiratory connector to the s-shaped tubular airway device;

a retention member positioned on the s-shaped tubular airway device and extending circumferentially about and coaxially along the elongate body portion of the s-shaped tubular airway device the retention member having a length and including a plurality of substantially uniformly spaced-apart ribs positioned axially along the length of the retention member and extending radially outwardly therefrom, the retention member further including a plurality of structural recesses positioned axially along the length of the retention member, each of the plurality of structural recesses being positioned intermediate an adjacent two of the plurality of substantially uniformly spaced-apart ribs;

a securing device being a single continuous piece of material adapted to be secured to the patient, the securing device including a stabilizer having an upper or top surface, a lower or bottom surface, and a generally cylindrically-shaped bite block extending in a substantially perpendicular direction from the bottom surface coaxially with the central axis, the generally cylindrically-shaped bite block a body portion having a length, an outer surface and an inner surface defining a cylindrically shaped cavity about the central axis, a plurality of substantially uniformly spaced-apart annular flanges positioned axially along the inner surface of the body portion of the generally cylindrically-shaped bite block and extending substantially inwardly therefrom, a plurality of structural recesses positioned axially along the inner surface of the body portion of the generally cylindrically-shaped bite block intermediate an adjacent two of the plurality of substantially uniformly spaced-apart annular flanges, respectively, each one of the plurality of substantially uniformly spaced-apart annular flanges cooperating with an adjacent one of the plurality of the plurality of substantially uniformly spaced-apart annular flanges to define one of the plurality of structural recesses of the generally cylindrically-shaped bite block, respectively, each of the plurality the plurality of substantially uniformly spaced-apart annular flanges defining an aperture, each aperture being of the same configuration, alignment and orientation, each aperture being adapted to receive the s-shaped tubular airway device;

a strap adapted to be releaseably secured about the patient's head and to releaseably secure the securing device to the patient.

2. The airway stabilization system of claim 1 wherein the respiratory connector comprises a tubular member having an air passage extending therethrough, an outlet portion, a flange portion extending radially outwardly from the outlet portion and having an outer diameter larger than the outlet portion and a connector portion extending distally from the flange portion, the connector portion being adapted to be removably attached to the central connector.

3. The airway stabilization system of claim 2 wherein the outlet portion of the respiratory connector includes a tubular wall having an inner diameter that is larger than the connector portion and a standard 15 mm connector outer diameter.

4. The airway stabilization system of claim 3 wherein the connector portion includes a threaded section adapted to be threadably fitted to the central connector.

5. The airway stabilization system of claim 4 wherein the threaded section comprises a threaded Luer-lock end.

6. The airway stabilization system of claim 2 wherein the central connector includes a proximal end portion having an attachment portion adapted to mate with the connector portion of the respiratory connector.

7. The airway stabilization system of claim 4 wherein the attachment portion includes a threaded section adapted to mate with the threaded section of the connector portion of the respiratory connector.

8. The airway stabilization system of claim 7 wherein the threaded section of the attachment portion comprises a threaded Luer-lock end.

9. The airway stabilization system of claim 1 further comprising a disc member operatively connected to the securing device, the disc member having an aperture formed therein of the same configuration, alignment and orientation as each aperture defined by each of the plurality of substantially uniformly spaced-apart annular flanges positioned axially along the inner surface of the body portion of the generally cylindrically-shaped bite block, the aperture of the disc member being adapted to receive the s-shaped tubular airway device and first and second coupling members adapted to connect the disc member to the securing device and to support the disc member at a level above the upper surface of the stabilizer, whereby the disc member is adapted to provide clearance for the patient's lips.

10. The airway stabilization system of claim 1 wherein each of the plurality of substantially uniformly spaced-apart ribs of the retention member includes a plurality of lobes extending radially outwardly from the retention member, each of the plurality of lobes cooperating with an adjacent one of the plurality of lobes to form an arcuate-shaped section therebetween.

11. The airway stabilization system of claim 10 wherein each of the apertures defined by the plurality of inwardly extending substantially uniformly spaced-apart annular flanges of the bite block includes a plurality of spaced apart, radially outwardly extending arcuate peaks, each of the plurality of arcuate peaks being separated from one another by one of a plurality of arcuate lobe recesses, each of the plurality of arcuate peaks and arcuate lobe recesses being structured and arranged to form a mirror image of the shape of each of the plurality of substantially uniformly spaced-apart ribs of the retention member.

12. The airway stabilization system of claim 11 wherein the securing device is adapted to slideably receive the s-shaped tubular airway device and retention member when the s-shaped tubular airway device and retention member are rotatably positioned to align the plurality of lobes extending radially outwardly from the retention member with the plurality of radially outwardly extending arcuate peaks of the securing device.

13. The airway stabilization system of claim 12 wherein each of the plurality of radially outwardly extending lobes of the retention member further includes a tip and wherein each of the plurality of arcuate lobe recesses of the apertures defined by each of the plurality of inwardly extending substantially uniformly spaced-apart annular flanges of the securing device is adapted to operatively engage a respective one of the lobe tips of the retention member upon rotation of the securing device relative to the s-shaped tubular airway device, the securing device and the retention member each being adapted to actively engage one another circumferentially at multiple points of contact along the length of the body portion of the bite block, whereby the s-shaped tubular airway device is adapted to be locked in a preselected position relative to the patient's vocal cords.

14. The airway stabilization system of claim 1 further including a balloon secured to the distal end of the s-shaped tubular airway device and an inflation system adapted to inflate the balloon to a preselected pressure range and to monitor and to maintain the pressure within the preselected range.

15. The airway stabilization system of claim 14 wherein the s-shaped tubular airway device further includes a vocal cord locator band located at the distal end of the elongate body portion proximal to the balloon.

16. The airway stabilization system of claim 15 wherein the inflation system comprises:
  a first inflation lumen formed in the continuous sidewall of the s-shaped tubular airway device and extending from the proximal end of the s-shaped tubular airway device a length of the s-shaped tubular airway device's elongate body portion to the distal end of the s-shaped tubular airway device;
  at least one ingress aperture extending through the continuous sidewall at the distal end of the s-shaped tubular airway device to the first inflation lumen, the at least one ingress aperture being adapted to provide a passage for inflation air into the balloon;

an inflation system receptacle formed in the central connector, the inflation system receptacle being adapted to connect the inflation system to a source of inflation air; and a second inflation lumen formed in an inner wall section of the central connector, the second inflation lumen being connected at a first end to the inflation system receptacle and connected at a second end to the first inflation lumen.

17. The airway stabilization system of claim 16 further including an inflation manometer having an inlet adapted to be connected to the source of inflation air and an outlet, the outlet including a fastening section adapted to be removably attachable to the inflation system receptacle.

18. The airway stabilization system of claim 17 wherein the inflation manometer further includes a one-way valve operatively connected to the inlet, a pressure sensor operatively connected to the one-way valve via a conduit and to the outlet, the pressure sensor being adapted to monitor the pressure in the conduit and in the balloon.

19. The airway stabilization system of claim 18 further including a display adapted to display the pressure in the conduit.

20. The airway stabilization system of claim 19 wherein the outlet includes a fastening section adapted to be removably attached to the inflation system receptacle, whereby an air-tight connection is formed between the manometer and the inflation system receptacle.

* * * * *